United States Patent [19]

Cunningham et al.

[11] Patent Number: 5,429,930
[45] Date of Patent: Jul. 4, 1995

[54] KINETIC ENZYME ASSAY FOR DETERMINING THE $CO_2$ CONTENT OF BODY FLUIDS USING PEP CARBOXYLASE WITH INHIBITOR

[75] Inventors: Bryce A. Cunningham, Coralville; George F. Johnson; Rubio R. Punzalan, both of Iowa City, all of Iowa

[73] Assignee: Bio-Research Products, Inc., Coralville, Iowa

[21] Appl. No.: 119,586

[22] Filed: Sep. 13, 1993

Related U.S. Application Data

[63] Continuation of Ser. No. 820,617, Feb. 7, 1992, abandoned, which is a continuation-in-part of Ser. No. 383,851, Jul. 21, 1989, abandoned.

[51] Int. Cl.[6] .......................... C12Q 1/48; C12Q 1/32; C12N 9/10; C12N 9/88
[52] U.S. Cl. ........................................ 435/15; 435/4; 435/26; 435/188; 435/194; 435/232
[58] Field of Search .......................... 435/4, 15, 26, 183, 435/188, 194, 232, 808

[56] References Cited

U.S. PATENT DOCUMENTS

| | | | |
|---|---|---|---|
| 3,974,037 | 8/1976 | Adams | 435/26 |
| 3,977,944 | 8/1976 | Müller-Mathesium | 435/10 |
| 5,112,740 | 5/1992 | Nealon et al. | 435/15 |

FOREIGN PATENT DOCUMENTS 0076478  1/1986  European Pat. Off. .

OTHER PUBLICATIONS

Norris et al., "Colorimetric Enzymatic Determination of Serum Total Carbon Dioxide, as Applied to the Vichers Multichannel 300 Discrete Analyser", Clin. Chem. 21(8) 1093–1103, 1975.
Czeriome et al., "Quantification of Analyte and Interferent by Multipoint Analysis", Clin. Chem. 32(9) 1648–1654, 1986.
The Merck Index, p. 1336 #9167, 1983.
Johnson et al., Abstract #132 Clin Chem 30(6), 1984.
Chem. Abstracts; vol. 73, No. 25, Dec. 31, 1970, No. 12719c.

Primary Examiner—William H. Beisner
Assistant Examiner—Nancy J. Degen
Attorney, Agent, or Firm—Hovey, Williams, Timmons & Collins

[57] ABSTRACT

An improved kinetic assay is provided for spectrophotometrically determining the dissolved carbon dioxide ($CO_2$) content of a body fluid (e.g., blood, plasma or serum), wherein at about pH 8.0 the $CO_2$ is present substantially as bicarbonate ion ($HCO_3^-$). The assay sample is first subjected to a coupled reaction mixture containing phosphoenolpyruvate (PEP) and phosphoenolpyruvate carboxylase (PEPC) which enzymatically catalyzes conversion of $HCO_3^-$ to oxaloacetate (OA). The OA produced is subjected to a second coupled reaction mixture containing nicotinamide adenine dinucleotide (NADH) and malate dehydrogenase (MDH) which thereby reduces the OA to malate and oxidizes the NADH to $NAD^+$. The $CO_2$ level in the body fluid sample may indirectly be determined by spectrophotometrically measuring the change in NADH concentration. According to the invention, an amount of an inhibitor is added to the reaction mixture which renders the reaction kinetics of the system essentially first order over the entire bicarbonate concentration range of interest. A useful inhibitor substantially satisfies a model represented by the monoexponential equation $$A_t = (A_o - A_\infty)e^{-kt} + A_\infty \qquad [I]$$

A sufficient quantity of the inhibitor is present to substantially cause the coupled reactions to follow the model equation [I] and yield a number which is within about ±200% of the noise level of the spectrophotometer used for the assay when each absorbance value is applied to the equation $$SD^2_{est} = \frac{\Sigma (A_{obs} - A_{est})^2}{n - 3} \qquad [II]$$

Best results have been obtained through use of an inhibitor which provides an anion selected from the group consisting of $ClO_3^-$, $ClO_4^-$, $SCN^-$, or $I^-$.

21 Claims, 2 Drawing Sheets

KINETIC ENZYME ASSAY FOR DETERMINING THE CO₂ CONTENT OF BODY FLUIDS USING PEP CARBOXYLASE WITH INHIBITOR

This application is a continuation of application Ser. No. 07/820,617, filed Feb. 7, 1992, now abandoned, which is a continuation-in-part of Ser. No. 07/383,851, filed Jul. 21, 1989, now abandoned.

BACKGROUND OF THE INVENTION

1. Field of the Invention

The present invention is broadly concerned with an improved process for the accurate spectrophotometric determination of dissolved carbon dioxide ($CO_2$) in a sample, such as blood, plasma or serum. More particularly, it is concerned with such a process making use of the reaction between phosphoenolpyruvate (PEP) and bicarbonate ion ($HCO_3^-$) as catalyzed by phosphoenolpyruvate carboxylase (PEPC) to produce oxaloacetate (OA), followed by the indirect determination of the rate of production of OA. A nontoxic enzyme inhibitor is added which renders the kinetics of the system essentially first order over the entire $HCO_3^-$ concentration range of interest. Best results have been obtained when the inhibitor provides a $ClO_3^-$, $ClO_4^-$, $SCN^-$, or $I^-$ anion.

2. Description of the Prior Art

Analysis of body fluids such as blood serum for total dissolved $CO_2$ content is a widely employed test, useful in determining the acid-base status of a patient. It is also used to monitor patients in renal failure or acute acidosis. Generally speaking, the bicarbonate ion concentration in blood serum or plasma is from about 22 to 32 mmol/L, and under abnormal conditions may range between about 15 to 40 mmol/L. Accordingly, accurate dissolved $CO_2$ determinations of unknown samples within these concentration ranges is a matter of concern.

In general, prior $CO_2$ determinations have included manometric, pH indicator, spectrophotometric, and pH related electrode techniques, all of which require acidification of the sample. In addition, enzymatic spectrophotometric methods have been described in which the various forms of $CO_2$ in the sample are converted to $HCO_3^-$ under alkaline conditions; thereupon, the $HCO_3^-$ is converted to OA, the latter being indirectly measured by consumption of the reduced form of nicotinamide adenine dinucleotide (NADH) and quantitated spectrophotometrically.

In more detail, the enzymatic $CO_2$ determination described in the prior art makes use of the following coupled reactions:

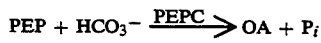

where PEPC is phosphoenolpyruvate carboxylase, $P_i$ is inorganic phosphate anion, OA is oxaloacetate, MDH is malate dehydrogenase and $NAD^+$ is the oxidized form of NADH. See, e.g., U.S. Pat. No. 3,974,037, which is incorporated by reference herein. As explained in that patent, the bicarbonate reacts with PEP in the presence of PEPC to quantitatively produce OA, whereupon the OA is measured as a function of conversion of NADH to the oxidized form thereof. NADH absorbs UV light between 320–400 nm, with an absorbance peak at 340 nm; $NAD^+$ on the other hand, has a negligible absorbance at these wave lengths. Accordingly, the conversion of NADH to the oxidized form thereof provides a convenient way to indirectly and quantitatively measure OA.

The foregoing coupled reactions can be used to determine $CO_2$ concentration by allowing the reactions to go to completion and measuring a total change in absorbance. This is referred to as an end point technique, but is not favored because it requires a large reagent-to-sample volume ratio to measure bicarbonate over a wide range of concentrations, and moreover it requires analyzers with high absorbance reading capabilities (low stray light and spectrophotometric noise). In spite of these factors, the end point determination is widely used because until now, a practical wide range kinetic method has not been available.

Alternatively, the $CO_2$ content of a sample may be determined as a function of how rapidly the enzymatic reaction converts the substrates to products. This rate determination or kinetic method depends on the principle that the rate of the reaction will be proportional to the concentration of a substrate converted by the reaction, where the concentration of the substrate limits the rate of the reaction. The basis of this principle is that, in an enzymatic reaction, the rate at which a substrate is converted to product depends both upon the basic physical rate of the enzyme catalyzed reaction and the frequency at which enzyme molecules and substrate molecules collide. The rate of collision is proportional to the concentration of substrate molecules. As substrate concentration is increased, frequency of collision reaches a maximum and is no longer a factor in determining reaction rate. At this substrate concentration, the concentration of substrate does not limit the rate at which the reaction can enzymatically proceed; only enzyme activity determines the rate of conversion of substrate molecules to product molecules.

Thus, in a rate determination of the content of a substrate in a sample, all other substrates participating in the reaction must be present at concentrations which do not limit the reaction rate, so that, insofar as substrates are concerned, only the concentration of the tested substrate is "rate-limiting". Accordingly, in the use of reaction [I] to kinetically determine $HCO_3^-$ in a sample, only the $HCO_3^-$ should be rate-limiting; PEP must be provided in amounts which do not limit the rate at which PEPC catalyzes the carboxylation of PEP to OA. Where reaction [I] is linked to reaction [II], NADH also must be provided in "non-rate-limiting amounts" and activity units of MDH must be sufficiently greater than the activity units of the PEPC employed so as to catalyze the rate of reaction [II] at a speed no slower than the rate of reaction [I]. Then, since the rate of formation of the OA limits the rate at which NADH is converted to NAD, and since the rate of formation of OA is in turn dependent upon the concentration of $HCO_3^-$ in the sample, spectrophotometric measurement of the NADH absorbance-decrease within a fixed time interval (i.e., the rate of absorbance change) can be used to determine the $HCO_3^-$ concentration in the sample.

In order to correlate a determined rate of absorbance change to the concentration of the substrate at which that rate occurs, it must be known whether the rate of absorbance change is directly proportional, or proportional in a more complex way, to the substrate concentration. This may be learned by repetitively conducting the same test, using the same reagents and under the same conditions, and making the rate of absorbance change measurements at the same fixed time interval, but varying the known concentrations of the substrate. These results are then plotted on a graph of substrate (X-axis) versus change in absorbance (Y-axis). If the relationship between the rate of absorbance change for the fixed time interval and the substrate concentration is linear between a selected zero point and the maximum substrate concentration desired to be determined, then only the rate of absorbance change for one known substrate concentration need be known in order to determine an unknown substrate concentration for which a rate of absorbance change is obtained under the same conditions and same fixed time interval. But if the plotted relationship between the rate of absorbance change and substrate concentration is not linear, resort must be made to the curve described by such relationship in order to determine an unknown substrate concentration corresponding to a measured rate of absorbance change. Such a standard curve is employed in methods exemplified by that described in the aforementioned U.S. Pat. No. 3,974,037. Stated otherwise, in such prior methods, the relationship between the rate of NADH absorption change and $HCO_3^-$ concentrations is not linear for all $HCO_3^-$ concentrations.

It is known that the rate equation for an enzymatic reaction may be expressed as:

$$v = \frac{V[S]}{K_m + [S]} \quad \text{[III]}$$

where v=rate of reaction, V=maximal velocity, [S]=substrate concentration, and $K_m$=the Michaelis-Menten constant. In the case of a true first order reaction, $K_m$ is much greater than [S], so that the latter term becomes negligible. However, in the system of interest, the $K_m$ and [S] values are of the same order of magnitude over the concentration range to be determined. As a consequence, the resulting absorbance plot is curvilinear.

In order to overcome this difficulty, it has been suggested in the past to employ a competitive inhibitor in the reaction system which has the effect of rendering the rate of the reaction linear or directly proportional to all concentrations of $HCO_3^-$ which could be found in a given body sample. For example, European Patent Specification 076,478 published Jan. 15, 1986 (this Specification being incorporated by reference herein) describes the use of inorganic pyrophosphates as inhibitors. In an inhibited system, it is known that the rate equation can be expressed as:

$$v = \frac{V[S]}{K_m(1 + [I]/K_i) + [S]} \quad \text{[IV]}$$

where v, V, [S] and $K_m$ are defined as set forth above, [I]=inhibitor concentration, $K_i$=inhibitor constant, and $K_m(1+[I]/K_i)$=apparent $K_m$. As can be appreciated from a study of equation [IV], a suitable inhibitor should be selected to make apparent $K_m$ much greater than [S], so that the resulting rate plot is linear.

While the noted European Patent Specification advocates the use of pyrophosphates as an appropriate inhibitor, others have found it difficult to replicate the results therein reported. Accordingly, there remains an unsatisfied need in the art for an inhibitor which will render the change in absorbance essentially linear over the $[HCO_3]^-$ concentration range of interest.

SUMMARY OF THE INVENTION

The present invention overcomes the problems outlined above, and provides an improved, inhibited enzymatic spectrophotometric assay for the determination of dissolved $CO_2$ concentration in body fluids, such as plasma or serum. Broadly speaking, the assay of the invention involves the steps of contacting a sample of body fluid with a reaction mixture having therein respective quantities of PEP and the enzyme PEPC, converting dissolved $CO_2$ to OA, and measuring (preferably indirectly) the rate of OA production. The system of the invention is inhibited by the presence of an inhibitor in the reaction mixture which renders the reaction kinetics of the system essentially first order over the entire bicarbonate range of interest. A useful inhibitor substantially satisfies a model represented by the monoexponential equation $$A_t = (A_0 - A_\infty)e^{-kt} + A_\infty \quad \text{[V]}$$

where $A_t$=the UV absorbance value at any point in time, $A_0$=the initial UV absorbance value, $A_\infty$=the UV absorbance value at essentially reaction completion, k=the first order rate constant for $HCO_3^-$ and at the concentration of the $HCO_3^-$ and enzyme respectively, t=the time at which the absorbance measurement is taken, and e=the natural log base value 2.718 . . . The $A_0$ and $A_\infty$ absorbance values and the first order rate constant k are established by calculation utilizing a standard nonlinear least squares statistical analysis. Infinity may be assumed to be about 12 minutes based on the fact that the reaction will have gone to virtual completion in a 12 minute time period under our stated conditions.

After fitting the reaction data to equation [V], the $SD^2_{est}$, the half life of the reaction and the rate constant of the reaction were determined. The $SD^2_{est}$ is the sum of the squares of differences between the observed absorbance change at every time point and the expected absorbance change as predicted by the model divided by (n−3). $SD^2_{est}$ thus serves as a measure of the fit of the reaction data to the first order model.

$$SD^2_{est} = \frac{(A_{obs} - A_{est})^2}{n - 3} \quad \text{[VI]}$$

where $A_{obs}$=the actual UV absorbance value obtained, $A_{est}$=the UV absorbance value which should be obtained in accordance with formula [V], and n=the number of observed UV absorbance values taken as individual data points.

An inhibitor which substantially causes the coupled reactions system [I] and [II] to follow the model equation [V] should yield a number for $SD^2_{est}$ of equation [VI] which is within about ±200% of the noise level of the spectrophotometer used for the assay when each absorbance value is applied to equation [VI].

Another method of ascertaining if an inhibitor adequately causes the enzymatic reaction to fit model equation [V] as applied to PEPC and $HCO_3^-$ involves carrying out a series of spectrophotometric measurements at increasingly higher $HCO_3^-$ concentrations and then plotting the change in the milliabsorbance values at a selected time period, for example, 60 seconds versus the concentration of $HCO_3^-$. If that plot yields a substantially straight line, then this is confirmation that the inhibitor is satisfactory.

Best results have been obtained when an inhibitor is used which provides anions selected from the group consisting of $ClO_3^-$, $ClO_4^-$, $SCN^-$, or $I^-$. Exemplary inhibitors in this respect include alkali metal and ammonium chlorates, perchlorates, iodides, and thiocyanates, with the potassium cation being preferred.

In terms of reaction mixture concentrations, the inhibitor should be present at a level of from about 30 to 300, and more preferably from about 60 to 100, mmol/L of the anion. When applied to the coupled reactions of equations [I] and [II], the inhibitor gives best results when present at a level of about 80 mmol/L of the anion.

The PEP fraction of the reaction mixture is preferably either monocyclohexyl- or tricyclohexyl ammonium PEP. This material should be present in the reaction system in an amount which will not limit the rate of reaction [I]. Typically, a non-rate limiting amount is at least 20 times the substrate $K_m$ for the enzyme. In the reaction mixture, the PEP should be present at a level of from about 2 to 10, and more preferably from about 3 to 6, mmol/L.

The PEPC enzyme should likewise be present in sufficient amounts and typically is employed at a level from about 0.2 to 1.0, and more preferably from about 0.6 to 0.9, U/ml, in the reaction mixture. Although PEPC is commercially available and can be derived from a number of plant tissues and microorganisms, wheat germ-derived enzyme is most preferred. One unit (U) of enzyme is equal to that amount which causes a change of 1 $\mu$mol of product in 1 minute at 30° C. using the conditions described by Iglesias and Andreo, *Biochim. Biophys. Acta*, Vol. 749, pp. 9–17 (1983). The treatise by Iglesias and Andreo specifically relates to maize systems. However, it has been found that their procedure as described is also optimal for wheat germ PEPC enzyme.

The rate of production of OA is normally determined using coupled reaction [II] described previously. For this purpose, the reaction mixture includes respective quantities of MDH and NADH. Reaction [II] must not proceed at a rate slower than reaction [I], so MDH is provided in activity units substantially in excess of the units of PEPC used. Suitably, this may be a ratio of 5 activity units of MDH per unit of PEPC. In the reaction mixture, the MDH is normally present at a level of from about 1 to 15, and more preferably from about 2.8 to 6.6 U/ml.

A non-rate limiting amount of NADH is also employed, bearing in mind the absorbance limit of the spectrophotometer to be employed. Generally, NADH is present at a level of from about 0.2 to 1.0, and more preferably from about 0.4 to 0.6 mmol/L in the reaction mixture, for a 0.5 cm path cell.

The present kinetic method allows NADH in the coupled reactions [I] and [II] to be employed at significantly lower levels than is the case in previous end point $CO_2$ measurement processes. For example, the NADH of this invention may be limited to levels which provide spectrophotometric absorbance values measured at 340 nm which are in the range of about 0.5 to 1.0 A. End point $CO_2$ determination procedures required an adequate amount of NADH in the assay solution to provide absorbance values measured at 340 nm in the range of at least about 1.5 to 2.0 A. This represents a cost saving by virtue of the fact that about one-half of the NADH is required in the present kinetic processes as compared with end point determination methods.

The preferred reaction mixtures of the present invention would also generally include a divalent metal enzyme cofactor, e.g., magnesium or manganese ion. Magnesium sulfate is preferably present at a level of from about 3 to 10 mmol/L in the reaction mixture. Additionally, a quantity of sodium oxamate (a lactic dehydrogenase inhibitor) may be used if desired but is not necessary. N-acetylcysteine (a sulfhydryl reagent) is also added with the acetylcysteine, and oxamate, if used, being added at levels of from about 1.0 to 1.5 and 1.0 to 1.5 mmol/L in the reaction mixture.

The bicarbonate in a sample of body fluid is determined by forming the described reaction mixture containing the unknown sample, and also forming a second reaction mixture by combining all of the described reagents with a sample containing a known concentration of $HCO_3^-$. Measurements of the decrease in absorbance of each of these mixtures is made after the same lapsed time at the same wave length (typically 340 mm) and at the same fixed time interval, while maintaining both mixtures at substantially constant temperatures and basic pH levels. There is then applied to the measured absorbance decrease of the unknown reaction mixture, a factor in which the numerator is the known $HCO_3^-$ concentration of the known sample and in which the denominator is the measured absorption decrease of the known reaction mixture.

In practice, the temperature conditions during analysis should be maintained from about 20°–50° C. and more preferably about 30°–37° C. Levels of pH should be about 7–9, more preferably about 8.

DESCRIPTION OF THE PREFERRED EMBODIMENTS

EXAMPLE I

Figure 1:
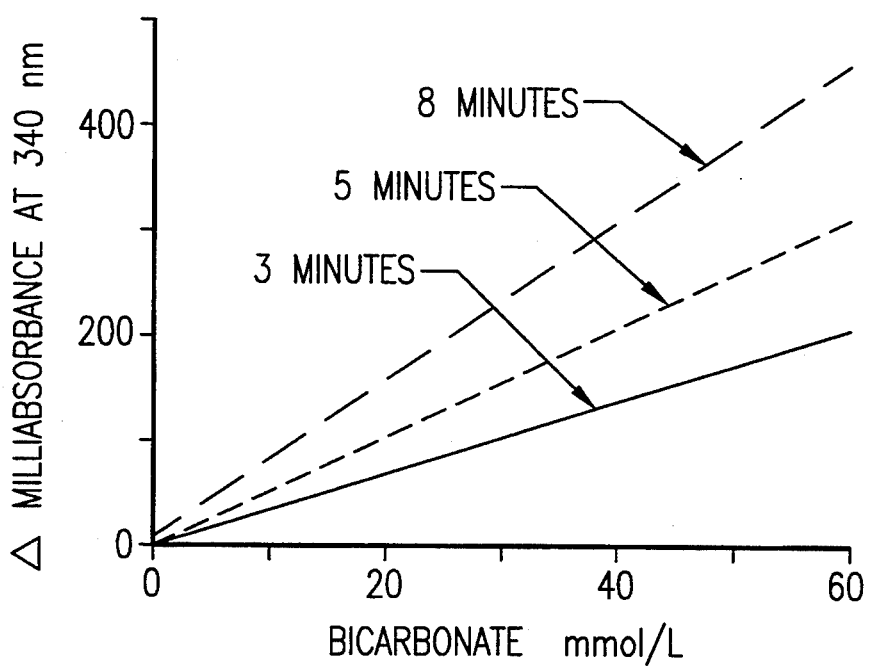
FIG. 1 is a set of representative concentration-absorbance change curves illustrating the linear response achieved through use of a thiocyanate inhibitor, wherein the change in milliabsorbance ($\Delta$milli A) is defined as $10^3$ times the absorbance change between 3 seconds and the indicated times.

The dissolved $CO_2$ assay of the present invention can advantageously be performed as follows, in the case of serum determinations. The procedure described should not be considered a limitation upon the overall scope of the invention.

In particular, two stock solutions, namely an enzyme solution (reagent 1) and a coenzyme solution (reagent 2), are prepared along with a known and an unknown substrate solution. The constituents of these solutions are set forth below:

| Enzyme Diluent | |
|---|---|
| Morpholinopropanesulfonic acid/NaOH, pH 7.2 | 20 mmol/L |
| MgSO$_4$ | 2 mmol/L |
| N-acetylcysteine | 2 mmol/L |
| Glycerol | 30% v/v |
| Reagent 1 (Enzyme Solution) | |
| Enzyme diluent | 3.73 mL |
| PEPC (14 U/mL stock solution) | 369 μL |
| MDH (10,000 U/mL in glycerol) | 5.2 μL |
| NADH (24 mmol/L) | 100 μL | yielding a final volume of 4.2 mL. The concentrations of PEPC, MDH and NADH in Reagent 1 are as follows: PEPC-1.2 U/mL; MDH (porcine)-12.4 U/mL; and NADH-0.6 mmol/L.

| Reagent 2 (Coenzyme Solution) | |
|---|---|
| MgSO$_4$ | 49.2 mmol/L |
| PEP (tricyclohexyl ammonium) | 39.2 mmol/L |
| N-acetylcysteine | 12.2 mmol/L |
| KSCN | 480 mmol/L |
| Na tricine (Buffer, pH 8.0) | 50 mmol/L |

Three μL of the sample to be analyzed, 22 μL of water as a diluent, and 50 μL of reagent 2 were loaded into the inner circumferentially extending well of the rotor of a Multistat III Plus System centrifugal/analyzer commercialized by Instrumentation Laboratories. The device includes a rotor having multiple sample sections each provided with inner and outer chambers separated by an inclined ramp. During rotation, centrifugal force serves to move the material from each inner chamber upwardly over a respective ramp and ultimately into contact with the materials in the corresponding outer chamber to effect mixing of the reactants. 200 μL of reagent 1 and 25 μL of water as a diluent were loaded into the outer wells of the same rotor to give a total liquid volume of 300 μL in each chamber of the rotor. The rotor was transferred into the analyzer, incubated for 4 minutes at 37.0° C. centrifuged to mix the solutions, and analyzed by taking absorbance readings at 340 nm. The initial reading is taken at 3 seconds and at 15 second intervals thereafter.

In a preferred analysis, the final concentrations of each of the components mixed in the spectrophotometric measurement cuvette were as follows: PEPC—0.82 U/mL; NADH—0.38 mmol/L; MgSO$_4$—8 mmol/L; N-acetylcysteine —2 mmol/L; PEP—6.5 mmol/L; KSCN—80 mmol/L. The bicarbonate levels were varied from 0.5 mmol/L to 50 mmol/L.

EXAMPLE II

Comparison of Non-linear Regression Model Parameters For Reactions With and Without KSCN Inhibitor

| HCO$_3^-$ (mmol/L) | SD$^2_{est}$ milliabsorbance (milli A) | | T$_{\frac{1}{2}}$ (half life seconds) | | k × 10$^3$ (1/sec) | |
|---|---|---|---|---|---|---|
| | a | b | a | b | a | b |
| 4 | 1.7 | 1.9 | 148 | 15 | 4.67 | 45.4 |
| 9 | 1.1 | 1.9 | 148 | 18 | 4.70 | 38.2 |
| 20 | 1.5 | 4.4 | 147 | 20 | 4.72 | 34.5 |
| 30 | 1.8 | 9.1 | 145 | 22 | 4.62 | 31.7 |
| 38 | 3.5 | 12.2 | 152 | 23 | 4.55 | 30.1 |
| 45 | 3.7 | 28.9 | 155 | 26 | 4.46 | 26.6 |

(a) 80 mmol/L KSCN
(b) This column refers to the reaction without KSCN

The differential effect with and without the KSCN inhibitor is most observable at higher bicarbonate concentrations as is evident from the table of this Example.

EXAMPLE III

Comparison of Non-linear Regression Model Parameters for Reaction With KI Inhibitor (80 mmol/L)

| HCO$_3^-$ (mmol/L) | SD$^2_{est}$ milliabsorbance (milli A) | T$_{\frac{1}{2}}$ (half life seconds) | k × 10$^3$ (1/sec) |
|---|---|---|---|
| 20 | 2.3 | 57.8 | 12 |

EXAMPLE IV

Comparison of Non-linear Regression Model Parameters for Reaction With KClO$_3$ Inhibitor (60 mmol/L)

| HCO$_3^-$ (mmol/L) | SD$^2_{est}$ milliabsorbance (milli A) | T$_{\frac{1}{2}}$ (half life seconds) | k × 10$^3$ (1/sec) |
|---|---|---|---|
| 20 | 2.8 | 57.8 | 24 |

EXAMPLE V

Comparison of Non-linear Regression Model Parameters for Reaction With KClO$_4$ Inhibitor (85 mmol/L)

| HCO$_3^-$ (mmol/L) | SD$^2_{est}$ milliabsorbance (milli A) | T$_{\frac{1}{2}}$ (half life seconds) | k × 10$^3$ (1/sec) |
|---|---|---|---|
| 20 | .6 | 104 | 6.3 |

EXAMPLE VI

Another and less preferred example of carrying out a dissolved CO$_2$ spectrophotometric assay of a serum sample employs two stock solutions, namely an enzyme and coenzyme solution, along with a known and an unknown substrate solution. The constituents of these solutions are set forth below:

| Enzyme Solution | |
|---|---|
| PEPC (wheat germ) | 2 U/ml |
| MDH (porcine) | 20 U/ml |
| Buffer (Na Tricine, pH 8.0) | 10 mmol/L |
| Coenzyme Solution | |
| MgSO$_4$ | 20 mmol/L |
| PEP (Tricyclohexyl ammonium) | 16 mmol/L |
| N-acetylcysteine | 5 mmol/L |
| Sodium oxamate | 5 mmol/L |
| NADH | 2 mmol/L |
| Buffer (Na Tricine, pH 8.0) | 10 mmol/L |
| Substrate Solution | |
| Bicarbonate sample | variable |
| KSCN | 10 mol/L |

| -continued | |
|---|---|
| Buffer (Na Tricine, pH 8.0) | 10 mmol/L |

The known substrate solution contained a predetermined concentration of bicarbonate ion and thus served as the system standard, whereas the unknown substrate solution was used to determine bicarbonate concentration. The determination was again carried out using the Multistat III Plus System centrifugal/analyzer.

Respective sample sections of the inner chamber of the instrument were loaded with the known and unknown substrate solutions. Each of these substrate solutions consisted of 5 μL of serum, 4 μL of 10M potassium thiocyanate inhibitor and 10 μL of degassed distilled water. The corresponding sample sections of the outer chamber of the device were loaded with respective solutions each comprising a 1:1 volumetric mixture of the described enzyme and coenzyme solutions, together with additional buffer. Specifically, each of the outer chamber solutions included 50 μL of enzyme solution, 50 μL of coenzyme solution, and 81 μL of degassed distilled water, for a total of 181 μL. This combined solutions were immediately loaded after preparation so as to minimize reaction with $CO_2$ from the air.

Figure 2:
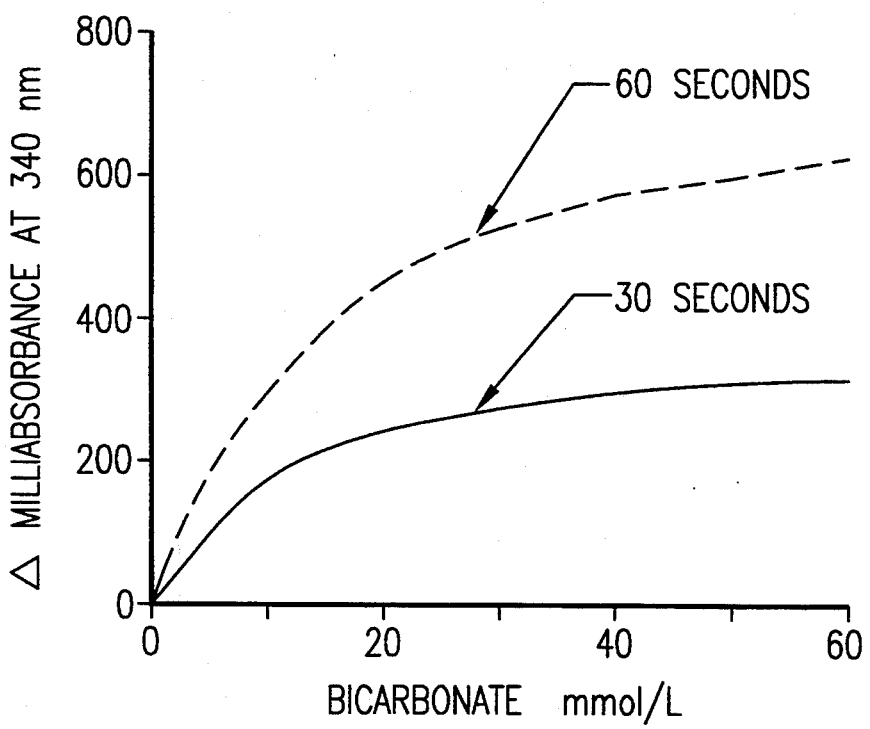
FIG. 2 is a set of representative concentration-absorbance change curves illustrating the non-linear response of the system depicted in FIG. 1, in the absence of a thiocyanate inhibitor, and wherein the data is set forth as explained in connection with FIG. 1.

After the centrifugal analyzer was loaded with the solutions described above, they were allowed to incubate at 37° C. for five minutes. Thereupon, the solutions were mixed by centrifugal force and the reaction was allowed to run for three to eight minutes. Absorbance change readings were at a time of 30 to 60 seconds for solutions without an inhibitor (FIG. 2), and at times from three to eight minutes for solutions with inhibitor as depicted in FIG. 1. The incubation times with an inhibitor are longer than without an inhibitor because of the slower enzymatic reaction when an inhibitor is present. Absorbance readings at 340 nm were taken during spinning at the conclusion of the selected time period. For this purpose the device was provided with a spectrophotometer port adjacent the outer chamber. The fixed time absorbance change readings for the known and unknown reaction mixtures were then be used to directly calculate the dissolved $CO_2$ concentration in the unknown. Specifically, the concentration of the $HCO_3^-$ in the unknown was determined by applying to the measured decrease in absorbance of the unknown reaction mixture a factor in which the numerator is the $HCO_3^-$ concentration of the known reaction mixture and in which the denominator was the measured absorbance decrease of the known reaction mixture.

Figure 4:
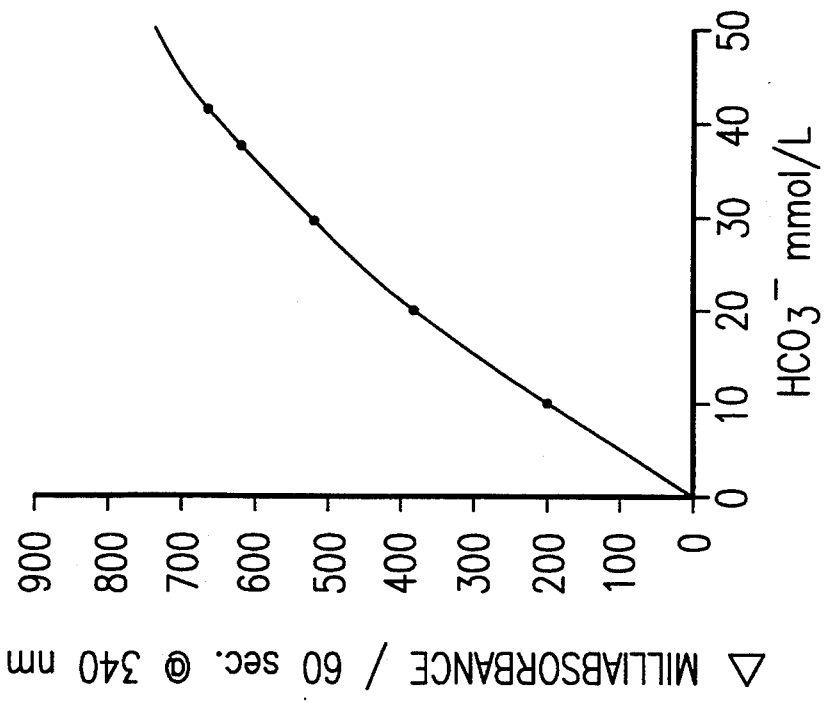
FIG. 4 is a representation similar to FIG. 1 but showing the results obtained when no inhibitor was added to the sample being tested.
Figure 3:
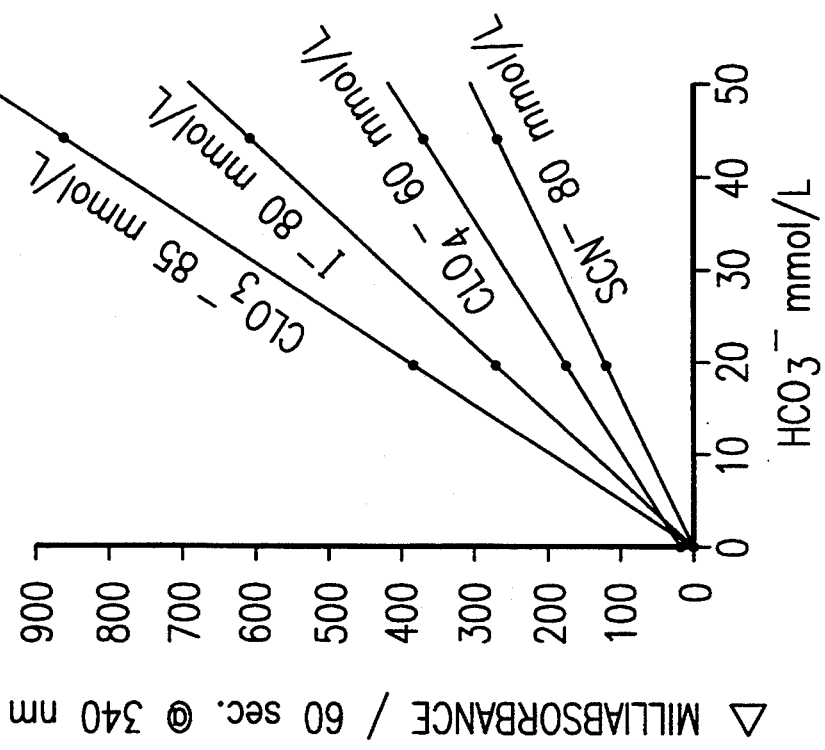
FIG. 3 is a set of representative concentration-absorbance change curves illustrating the linear response achieved through the use of the present assay utilizing inhibitors containing $ClO_3^-$, $ClO_4^-$, $SCN^-$, and $I^-$ anions respectively wherein the change in milliabsorbance values ($\Delta$milli A), obtained at 60 seconds with spectrophotometer readings taken at 340 nm are shown along the Y axis, while $HCO_3^-$ levels are plotted on the X axis.

As can be seen from FIGS. 1 and 3, use of anions selected from the group consisting of $ClO_3^-$, $ClO_4^-$, $SCN^-$, and $I^-$ generates essentially linear absorbance change curves over the concentration range of interest. In this fashion, accurate, repeatable dissolved $CO_2$ determinations can be readily made. Without an inhibitor of the present invention, however, the absorbance change curves are nonlinear and complex. Representative curves generated without inhibitor are set forth in FIGS. 2 and 4. These curves, together with those of FIGS. 1 and 3, were generated using known $HCO_3^-$ samples, and generation of absorbance data points during the centrifugation/reaction time. This data was then analyzed using a computer and multipoint kinetic curve fitting methods as described in "Quantification of Analyte and Interferent by Multipoint Analysis" *Clin Chem.*, 32:9, pp 1648-1654 (1986) by Czervionke, et al., this article being incorporated by reference herein. In any event, a study of FIGS. 2 and 4 will demonstrate that the standard curves generated in an uninhibited system are nonlinear and very quickly assume a generally flat configuration. This makes it very difficult to achieve accurate readings with the nonlinear graphs, and makes them unsuitable for routine laboratory use.

On the other hand, the inhibited system of the present invention can be readily employed in a laboratory without need for,generating complex curvilinear concentration-absorbance curves, and the invention has been shown to give accurate $CO_2$ determinations.

We claim:

1. In a kinetic assay for spectrophotometrically determining the dissolved $CO_2$ content of a body fluid using a spectrophotometer which may have an inherent noise level, said kinetic assay including the steps of contacting a sample of the body fluid where the dissolved $CO_2$ content is present substantially as $HCO_3^-$, with an overall assay reaction mixture including a first coupled assay reaction mixture having therein individual quantities of a phosphoenolpyruvate (PEP) and phosphoenolpyruvate carboxylase (PEPC), to convert the $HCO_3^-$ present to oxaloacetate (OA) which is thereafter reduced by a second coupled reaction mixture containing nicotinamide adenine dinucleotide (NADH) and malate dehydrogenase (MDH), to effect reduction of the OA to malate (M) and oxidation of the NADH to $NAD^+$, whereby the dissolved $CO_2$ content of the body fluid sample may be indirectly spectrophotometrically determined by the change in NADH concentration, the improvement of which comprises:

adding to the overall assay reaction mixture an inhibitor for the PEPC which causes the reaction of $HCO_3^-$ in the sample with the PEPC to substantially satisfy a model represented by the monoexponential equation $$A_t = (A_0 - A_\infty)e^{-kt} + A_\infty \qquad \text{[I]}$$

where $A_t$=the UV absorbance value at any point in time, $A_0$=the initial UV absorbance value, $A_\infty$=the UV absorbance value at essentially complete reaction, k=the first order reaction rate constant, t=the time at which the absorbance measurement is taken, and e=the natural log base value 2,718 . . . , the $A_0$ and $A_\infty$ absorbance values and the first order rate constant k having been established by a non-linear least squares statistical analysis, said inhibitor in the amount employed serving to modify the kinetics of said assay in such manner that a graph of the change in absorbance versus bicarbonate levels at selected times for the assay gives an essentially linear plot passing substantially through the 0,0 origin of the graph, a sufficient quantity of the inhibitor being present to substantially cause the coupled reactions to follow the mono-exponential equation [I] and yield a number which is within about ±200% of said inherent noise level of the spectrophotometer used for said kinetic assay when each absorbance value is applied to the equation $$SD^2_{est} = \frac{\Sigma (A_{obs} - A_{est})^2}{n - 3} \qquad \text{[II]}$$

where $A_{obs}$=the actual UV absorbance value obtained, $A_{est}$=the UV absorbance value which should be obtained in accordance with equation [I], and n=the number of observed UV absorbance values taken as individual data points.

2. The assay of claim 1, where said inhibitor causes the half life of the $HCO_3^-$—PEPC reaction to be relatively constant.

3. The assay of claim 1, wherein a plot of observed UV absorbance values taken of the body fluid sample is substantially linear where one axis of the plot represents mmol/L of $HCO_3^-$ and the other axis represents the differences in observed UV absorbances.

4. The assay of claim 1, wherein said inhibitor is selected from a group which provides anions selected from the group consisting of $ClO_3^-$, $ClO_4^-$, $SCN^-$, and $I^-$.

5. The assay of claim 4, wherein said inhibitor is present at a level to provide from about 30 to about 300 mmol/L of the anion.

6. The assay of claim 4, wherein said inhibitor is present at a level to provide from about 60 to about 100 mmol/L of the anion.

7. The assay of claim 4, wherein said inhibitor is present at a level of about 80 mmol/L of the anion.

8. The assay of claim 4, wherein said PEPC is present at a level of from about 0.2 to about 1.0 U/mL.

9. The assay of claim 8, wherein said PEPC is present at a level of from about 0.6 to about 0.9 U/mL.

10. The assay of claim 1, wherein said inhibitor provides an $SCN^-$ anion.

11. The assay of claim 1, wherein said inhibitor provides an $ClO_3^-$ anion.

12. The assay of claim 1, wherein said inhibitor provides an $ClO_4^-$ anion.

13. The assay of claim 1, wherein said inhibitor provides an $I^-$ anion.

14. The assay of claim 1, wherein the inhibitor is selected from the group consisting of alkali metal and ammonium thiocyanates.

15. The assay of claim 14, wherein the inhibitor is potassium thiocyanate.

16. The assay of claim 1, said body fluid being selected from the group consisting of plasma and serum.

17. The assay of claim 1, said phosphoenolpyruvate being selected from the group consisting of the alkali metal phosphoenolpyruvates, and the monocyclohexyl- and tricyclohexyl ammonium phosphoenolpyruvates.

18. The assay of claim 1, said overall assay reaction mixture including therein magnesium ion and N-acetylcysteine.

19. The assay of claim 1, said overall assay reaction mixture being buffered to a pH of from about 7 to 9.

20. The assay of claim 19, said pH being about 8.

21. The assay of claim 1, said PEPC enzyme being derived from wheat.

* * * * *